United States Patent [19]

Guth et al.

[11] Patent Number: 5,968,330

[45] Date of Patent: Oct. 19, 1999

[54] ELECTRODE MATERIAL

[75] Inventors: Ulrich Guth, Greifswald; Steffen Jakobs, Neuenkirchen; Edelbert Häfele, Karlsruhe, all of Germany

[73] Assignee: Heraeus Electro-Nite International N.V., Houthalen, Belgium

[21] Appl. No.: 09/046,167

[22] Filed: Mar. 23, 1998

[30] Foreign Application Priority Data

Mar. 24, 1997 [DE] Germany .......................... 197 12 315

[51] Int. Cl.$^6$ .................................................. G01N 27/26
[52] U.S. Cl. ........................ 204/424; 204/421; 422/94; 422/98
[58] Field of Search ..................... 204/421, 424, 204/400; 422/83, 94, 98; 429/40; 423/594, 595, 596, 600, 606, 607, 624, 625, 632, 633, 635; 505/776, 777, 778, 779, 780, 781; 501/152, 153, 123, 126; 252/513, 519.15, 520.5, 521.1, 521.2

[56] References Cited

U.S. PATENT DOCUMENTS 4,454,494 6/1984 Williams et al. .......................... 422/94
5,015,616 5/1991 Sekido et al. .............................. 422/94
5,616,223 4/1997 Shen et al. ................................ 204/421
5,863,503 1/1999 Kudo et al. ................................ 422/94

*Primary Examiner*—Bruce F. Bell
*Attorney, Agent, or Firm*—Akin, Gump, Strauss, Hauer & Feld, L.L.P.

[57] ABSTRACT

An electrode material is provided for electrochemical sensors, particularly for sensors detecting combustible gases. For these types of applications, perovskite electrode materials are known which, however, by modification of their oxygen stoichiometry, have a considerable charge carrier mobility. These defects are the causes for an additional, catalytic activity with oxidation processes at electrodes. The measurement of hydrocarbons from combustible gases is thus distorted with electrode materials of this type. These disadvantages are overcome by making such electrode materials from mixed oxides with non-perovskite crystalline structures, which have chemical compositions of one or more of the following general formulas: $(A/D)_{3-y}B_xC_{5-x}O_{12\pm\delta}$, $D_{1-y}B_{1-x}C_xO_{4\pm\delta}$, $D_{2-y}B_{8-x}C_xO_{16\pm\delta}$, $D_{2-y}B_{1+x}C_{1-x}O_{5\pm\delta}$, or $D_{2-y}B_xC_{2-x}O_{7\pm\delta}$, wherein A and D are respectively sub-stoichiometrically used cations of the lanthanide series and the alkaline earth metal group, A/D means a cation selected from A, D and mixture thereof, B is a multivalent ion, and C is a redox-stable ion.

10 Claims, No Drawings

ELECTRODE MATERIAL

BACKGROUND OF THE INVENTION

The invention involves an electrode material for electrochemical sensors made of a mixed oxide.

The concentration of unburned combustibles in oxygen-containing gases can be determined by known means in situ in a combustion gas stream by sensors which have two electrodes on a solid electrolyte, e.g. yttrium-stabilized zirconium dioxide. The electrodes react to the measurement gas in different ways. The potential of one electrode is determined to a large extent by the equilibrium oxygen partial pressure of the gas, while the potential of the other electrode is determined predominantly by the partial pressure of the combustible gas, so that a voltage can be measured between the electrodes in the same gas, which voltage is a function of the hydrocarbon concentration. Preferably, gold and alloys of gold and platinum are used as $CH_x$ sensitive electrodes (See, for example, A. Vogel, G. Baier, V. Schüile, Sensors and Actuators 15-16, pages 147–150 (1993)).

It is disadvantageous in arrangements of this type, that gold electrodes are not stable over time in their morphology at the relatively high operating temperatures of the cells ($\geq 700$ ° C.), and as a result the potential adjusting to that is subjected to temporal changes. Another disadvantage is that when the stoichiometric ratio ($\lambda=1$) of air to fuel is exceeded, a potential jump is observed which is more or less significant with electrodes of this sort. Moreover, the potential of electrodes of this type is a function of the pretreatment in regard to gas composition and temperature, so that memory effects can be observed, which must be eliminated by subsequent calibration when they are used in sensors.

Furthermore, mixed oxides of the perovskite type are known as electrode materials, which are generally used as oxygen electrodes. Preferably, only oxygen is electrochemically converted at electrodes of this type.

Moreover, perovskite electrode materials are known which are sensitive to the combustible gases. However, these mixed oxides of the perovskite type exhibit the following disadvantages:

By incorporation (e.g., by doping) of allovalent cations into perovskite type compounds of the general formula $ABO_3$ the oxygen stoichiometry often changes and vacancies in the oxygen sublattice occur, which exhibit considerable mobility. These defects are the cause for an additional, catalytic activity for oxidation processes. Solid electrolyte electrodes, which are constructed from this type of electrode material, convert hydrocarbons from combustible gases in a purely chemical manner using residual oxygen and thereby distort the measurement results.

SUMMARY OF THE INVENTION

In view of the aforementioned disadvantages of the prior art, an object of the invention is thus to create an electrode material for electrochemical sensors which is sensitive to combustible gases (e.g., fuel gases), which is redox stable and stable at high temperatures, and which has a sufficient electrical conductivity, at low catalytic activity, for use as an electrode material.

This object is achieved by an electrode material for electrochemical sensors, which comprises a mixed oxide having a non-perovskite type crystalline structure and having a chemical composition of one of the following general formulas: $(A/D)_{3-y}B_xC_{5-x}O_{12\pm\delta}$, $D_{1-y}B_{1-x}C_xO_{4\pm\delta}$, $D_{2-y}B_{8-x}C_xO_{16\pm\delta}$, $D_{2-y}B_{1+x}C_{1-x}O_{5\pm\delta}$, or $D_{2-y}B_xC_{2-x}O_{7\pm\delta}$, wherein A and D are respectively sub-stoichiometrically used cations of the lanthanide series and the alkaline earth metals group, respectively, and A/D means a cation selected from A, D and mixtures thereof, B is a multivalent ion, and C is a redox-stable ion. The possible metal oxide compounds characterized by the foregoing formulas correspond to the general compounds of the minerals: garnet ($A_3 B_5O_{12}$), scheelite (D B $O_4$), hollandite ($D_2B_8O_{16}$), brownmillerite ($D_2B_2O_5$), and pyrochlore ($D_2C_2O_7$).

The $\delta$ cited in the formulas stands for a possible charge compensation in the use of cations having different valences. Minor imperfections in the oxygen partial lattice are offset by an oxygen content increased or lowered by an amount $\delta$. The ion indicated as a multivalent ion B, which originates from the series of transition metals, should function as a source for electrons or holes. Using the valent-stable ion C, the concentration of electronic charge carriers can be adjusted. The sub-stoichiometrically inserted cation A and/or D in turn influences the concentration of the defect electrons and the oxygen vacancies.

By the combination of the aforementioned ion types in a non-perovskite mixed oxide having a chemical composition of one or more of the above general formulas, an almost complete anion lattice is created, having a slight mobility of the oxygen vacancies positions and thereby an associated low catalytic activity. The electrical conductivity is on the order of magnitude of the electrical conductivity of semi-conductors and thus makes it easier to adequately connect an electrode made of the electrode material according to the invention. Advantageous embodiments of the subject matter of the invention are set forth below and in the dependent claims.

DETAILED DESCRIPTION OF THE INVENTION

In the above general formulas for the chemical compositions of the electrode materials according to the present invention, the values of x and y are selected such that the cations A and/or D and at least one of the ions B and C is present in the mixed oxide in a significant amount, i.e., at least about 0.5 mole %. Preferably, y ranges from 0.005 to 0.4, and the range of x varies depending upon the particular compound. Thus, for compounds of the formula $(A/D)_{3-y}B_xC_{5-x}O_{12\pm\delta}$, x preferably ranges from 0.005 to 2.995; for compounds of the formula $D_{1-y}B_{1-x}C_xO_{4\pm\delta}$, x preferably ranges form 0.005 to 0.995; for compounds of the formula $D_{2-y}B_{8-x}C_xO_{16\pm\delta}$, x preferably ranges from 0.005 to 7.995; for compounds of the formula $D_{2-y}B_{1+x}C_{1-x}O_{5\pm\delta}$, x preferably ranges from 0.005 to 0.995; and for compounds of the formula $D_{2-y}B_xC_{2-x}O_{7\pm\delta}$, x preferably ranges from 0.005 to 1.995.

In the compounds of the invention, A in the general formula is a cation of an element in the lanthanide series, preferably lanthanum (La), yttrium (Y) or gadolinium (Gd). Alternative to or doped to or mixed with the lanthanide cation may be an alkaline earth group metal (represented by the letter D), such as calcium (Ca), magnesium (Mg) or strontium (Sr)).

The multivalent ion B may be an ion of a transition metal, preferably chromium (Cr), manganese (Mn), cobalt (Co), iron (Fe) or nickle (Ni). The redox-stable ion C is preferably selected from aluminum (Al), gallium (Ga), niobium (Nb) or tantalum (Ta).

The electrode materials of the present invention can be made according to the following principal process. The corresponding metal oxides, carbonates and/or nitrates from the groups of rare earth metals and/or alkaline earth metals and the transition metals are finely mixed in stoichiometric proportions, for example by comminution in a suitable milk. The addition of an organic solvent, such as cyclohexane, can be advantageous for this purpose. The comminuted fraction is then allowed to settle out, in order to dry it after decantation. Subsequently, there follows a calcination process, which for more thorough mixing, can be interrupted by a further comminution step. After the calcination there follows a repeated comminution, whereby a fine powder is obtained, which is further worked into a paste with the addition of a paste-forming material and/or solvent. This paste is applied to a substrate, for example in a screen printing process, and forms there an electrode after a burning-in step.

The following specific, non-limiting examples provide a more detailed explanation of the invention. The electrode material corresponds, for example, to compounds of the general formulas:

EXAMPLE 1

$A_{3-y}B_xC_{5-x}O_{12\pm\delta}$, wherein x=2, y=0.1 and A=lanthanum, B=iron, C=gallium, so that the electrode material comprises $La_{2.9}Fe_2Ga_3O_{12\pm\delta}$. Alternatively to the given compound, yttrium or gadolinium can be substituted as A, and chromium can be substituted for B.

EXAMPLE 2

$D_{2-y}B_{1+x}C_{1-x}O_{5\pm\delta}$, wherein x=0.4, y=0.2 and D=strontium, B=chromium, C=niobium, so that the electrode material comprises $Sr_{1.8}Cr_{1.4}Nb_{0.6}O_{5\pm\delta}$.

EXAMPLE 3

$A_{3-y}B_xC_{5-x}O_{12\pm\delta}$, wherein x=0.2, y=0.1 and A=gadolinium, B=chromium, C=gallium, so that the electrode material comprises $Gd_{2.9}Cr_{0.2}Ga_{4.8}O_{12\pm\delta}$.

EXAMPLE 4

$A_{3-y}B_xC_{5-x}O_{12\pm\delta}$, wherein x approximates 0, y=0.3 and A=gadolinium, C=gallium. An electrode material of the composition $Gd_{2.7}Ga_5O_{12\pm\delta}$ results which, as in Examples 1 and 3, has a crystalline structure corresponding to garnet.

The electrode materials set forth as examples are the so-called mixed conductors (i.e., electronically conducting/oxygen ion conducting), and thus are suitable as compounds for electrodes of electrochemical sensors, especially for combustion gas (fuel) sensing devices.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An electrode material for electrochemical sensors, comprising a mixed oxide having a non-perovskite crystalline structure and having a chemical composition of a general formula selected from the group consisting of:

$(A/D)_{3-y}B_xC_{5-x}O_{12\pm\delta}$, $D_{1-y}B_{1-y}C_xO_{4\pm\delta}$, $D_{2-y}B_{8-x}C_xO_{16\pm\delta}$, $D_{2-y}B_{8+x}C_{1-x}O_{5\pm\delta}$, and $D_{2-y}B_xC_{2-x}O_{7\pm\delta}$ wherein A and D are respectively sub-stoichiometrically used cations of the lanthanide series and the alkaline earth metal group, and A/D means a cation selected from A, D and mixtures thereof, B is a multivalent ion, and C is a redox-stable ion, x and y are selected such that A and/or D and at least one of B and C is present in the mixed oxide, and δ represents a possible charge compensation for minor imperfections in oxygen partial lattice of the crystalline structure.

2. The electrode material according to claim 1, wherein the multivalent ion B is a transition metal.

3. The electrode material according to claim 2, wherein the transition metal is selected from the group consisting of Cr, Mn, Co, Fe and Ni.

4. The electrode material according to claim 1, wherein the redox-stable ion C is selected from the group consisting of Al, Ga, Nb, and Ta.

5. The electrode material according to claim 1, comprising compounds of the general formula $(A/D)_{3-y}B_xC_{5-x}O_{12\pm\delta}$, wherein x ranges from 0.005 to 2.995.

6. The electrode material according to claim 1, comprising compounds of the general formula $D_{1-y}B_{1-x}C_xO_{4\pm\delta}$, wherein x ranges from 0.005 to 0.995.

7. The electrode material according to claim 1, comprising compounds of the general formula $D_{2-y}B_{8-x}C_xO_{16\pm\delta}$, wherein x ranges from 0.005 to 7.995.

8. The electrode material according to claim 1, comprising compounds of the general formula $D_{2-y}B_{1+x}C_{1-x}O_{5\pm\delta}$, wherein x ranges from 0.005 to 0.995.

9. The electrode material according to claim 1, comprising compounds of the general formula $D_{2-y}B_xC_{2-x}O_{7\pm\delta}$, wherein x ranges from 0.005 to 1.995.

10. The electrode material according to claim 1, wherein y ranges from 0.005 to 0.4.

* * * * *